United States Patent
Gharda et al.

(10) Patent No.: US 11,008,285 B2
(45) Date of Patent: May 18, 2021

(54) PROCESS FOR SYNTHESIS OF MESOTRIONE

(71) Applicant: GHARDA CHEMICALS LIMITED, Maharashtra (IN)

(72) Inventors: Keki Hormusji Gharda, Maharashtra (IN); Suchet Saran Mathur, Maharashtra (IN); Nandkumar Janardan Jain, Maharashtra (IN); Shekhar Vishwanath Sathe, Maharashtra (IN); Pragnesh Dalpatram Damania, Maharashtra (IN)

(73) Assignee: GHARDA CHEMICALS LIMITED, Maharashtra (IN)

( * ) Notice: Subject to any disclaimer, the term of this patent is extended or adjusted under 35 U.S.C. 154(b) by 0 days.

(21) Appl. No.: 16/498,233

(22) PCT Filed: Mar. 27, 2018

(86) PCT No.: PCT/IB2018/052076
§ 371 (c)(1),
(2) Date: Sep. 26, 2019

(87) PCT Pub. No.: WO2018/178860
PCT Pub. Date: Oct. 4, 2018

(65) Prior Publication Data
US 2020/0031767 A1    Jan. 30, 2020

(30) Foreign Application Priority Data

Mar. 27, 2017  (IN) .............................. 201721010839

(51) Int. Cl.
*C07C 315/04*  (2006.01)
*C07C 317/24*  (2006.01)
(52) U.S. Cl.
CPC .......... *C07C 315/04* (2013.01); *C07C 317/24* (2013.01)
(58) Field of Classification Search
CPC .... C07C 315/04; C07C 317/24; C07C 315/02
See application file for complete search history.

(56) References Cited

U.S. PATENT DOCUMENTS

| 5,055,605 A * | 10/1991 | Ludvik | C07C 315/02 560/11 |
| 5,424,481 A | 6/1995 | Hagen | |
| 5,886,231 A * | 3/1999 | Brown | C07C 45/54 568/310 |
| 7,820,863 B2 | 10/2010 | Wichert et al. | |
| 8,063,253 B2 | 11/2011 | Binder | |
| 2012/0165197 A1* | 6/2012 | Cohen | A01N 41/10 504/348 |
| 2016/0355472 A1 | 12/2016 | Bristow | |

OTHER PUBLICATIONS ("Heterogeneous photodegradation of mesotrione in nano α-Fe2O3/oxalate system under UV light irradiation", Royal Society of Chemistry, 2015, Issue 5, p. 12638-12643).*
International Search Report issued in co-pending International Application No. PCT/IB2018/052076 dated May 23, 2018.

* cited by examiner

*Primary Examiner* — Rosalynd A Keys
(74) *Attorney, Agent, or Firm* — Whiteford, Taylor & Preston, LLP; Peter J. Davis

(57) ABSTRACT

The present disclosure relates to a process for synthesis of mesotrione. The process comprises reacting 4-toluene sulfonyl chloride with alkali metal sulphite and alkali metal bicarbonate to obtain alkali metal toluene-4-sulfinate. The alkali metal toluene-4-sulfinate is reacted with alkali metal salt of monochloroacetic acid to obtain 4-methylsulfonyl toluene. Further, 4-methylsulfonyl toluene is nitrated to obtain 2-nitro-4-methylsulfonyl toluene. 2-nitro-4-methylsulfonyl toluene is oxidized and then halogenated to obtain 2-nitro-4-methylsulfonylbenzoyl halide. 2-nitro-4-methylsulfonylbenzoyl halide is reacted with alkali metal salt of 1,3-cyclohexanedione to obtain 3-(2-Nitro-4-methylsulfonylbenzoyloxy)cyclohexen-1-one which is reacted with base, a third fluid medium and cyanide ion source to obtain an amorphous mesotrione. The present disclosure also discloses the steps of converting the amorphous mesotrione to crystalline mesotrione having purity greater than 99%. The process of the present disclosure for preparing mesotrione is rapid, economic, and environment friendly.

18 Claims, 2 Drawing Sheets

PROCESS FOR SYNTHESIS OF MESOTRIONE

FIELD

Figure 1:
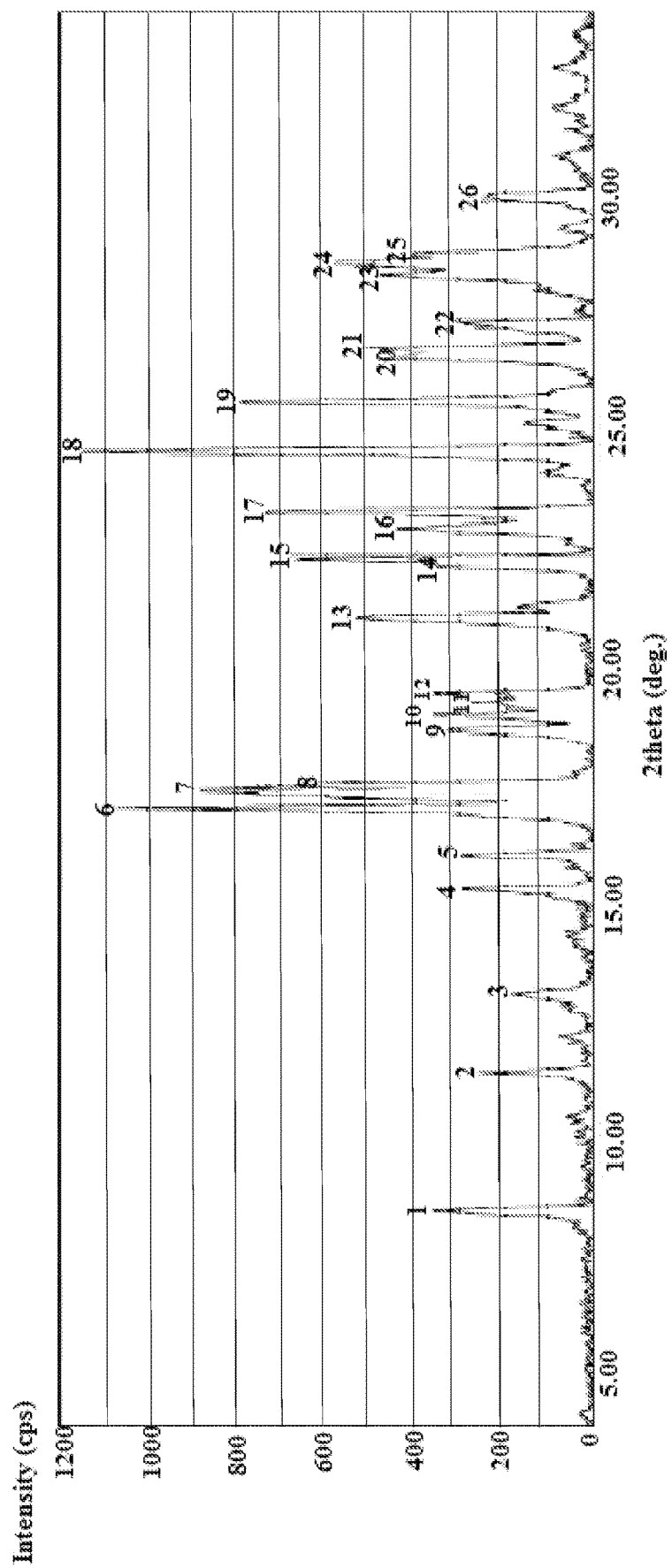

The present disclosure relates to a process for synthesis of mesotrione.

Definitions

As used in the present disclosure, the following terms are generally intended to have the meaning as set forth below, except to the extent that the context in which they are used indicate otherwise.

Crystalline Mesotrione: The term "Crystalline Mesotrione" refers to a thermodynamically stable form of mesotrione. The Crystalline Mesotrione is characterized by 2θ values: 8.57, 17.11, 17.49, 18.78, 19.09, 19.53, 21.16, 25.74, and 28.69.

Metastable form of Mesotrione: The term "Metastable form of Mesotrione" refers to a thermodynamically unstable form of mesotrione. The Metastable form of Mesotrione is characterized by 2θ values: 15.93, 16.99, 19.01, 20.55, 23.24, and 28.58.

BACKGROUND

The background information herein below relates to the present disclosure but is not necessarily prior art.

2-[4-(methanesulfonyl)-2-nitrobenzoyl]cyclohexane-1,3-dione is a second-generation triketone having the common name 'mesotrione'.

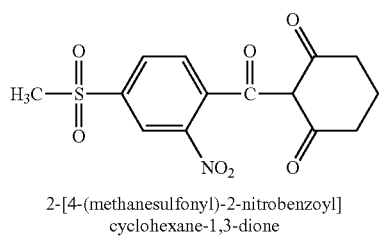 [SMILES: CS(=O)(=O)c1ccc(C(=O)C2C(=O)CCCC2=O)c([N+](=O)[O-])c1]

2-[4-(methanesulfonyl)-2-nitrobenzoyl]
cyclohexane-1,3-dione

Mesotrione is a selective herbicide for both pre-emergence and post-emergence control on most of the broadleaved weeds, and some grasses in maize and paddy rice. It is also used as herbicide for fruit plants such as berries, pome fruit, citrus fruits, some vegetables, sugar cane and turf.

Further, several processes for the synthesis of mesotrione are known in the art. However, the conventionally used reagents in the synthesis of mesotrione, are corrosive, and not environment friendly.

Therefore, there is felt a need for rapid, efficient, economical, and environment friendly process for synthesizing mesotrione.

OBJECTS

Some of the objects of the present disclosure, which at least one embodiment herein satisfies, are as follows.

It is an object of the present disclosure to ameliorate one or more problems of the prior art or to at least provide a useful alternative.

An object of the present disclosure is to provide a process for the synthesis of mesotrione which is rapid, economic and environment friendly.

Another object of the present disclosure is to provide a process for the synthesis of mesotrione having high yield.

Yet another object of the present disclosure is to provide a process for the synthesis of mesotrione having high purity.

Other objects and advantages of the present disclosure will be more apparent from the following description, which is not intended to limit the scope of the present disclosure.

SUMMARY

The present disclosure relates to a process for the synthesis of crystalline mesotrione. The process comprises the following steps:

In the first step, 4-toluenesulfonyl chloride is reacted with at least one alkali metal sulphite and at least one alkali metal bicarbonate, to obtain alkali metal toluene-4-sulfinate followed by reacting alkali metal toluene-4-sulfinate with at least one alkali metal salt of monochloroacetic acid to obtain 4-(methylsulfonyl)toluene.

The alkali metal sulphite is at least one selected from the group consisting of sodium sulphite, potassium sulphite and lithium sulphite. The alkali metal bicarbonate is at least one selected from the group consisting of sodium bicarbonate, potassium bicarbonate, and lithium bicarbonate. The molar ratio of 4-toluene sulfonyl chloride to alkali metal sulphite to alkali metal bicarbonate is in the range of 1:1:2 to 1:1.5:2.5. The alkali metal salt of monochloroacetic acid is at least one selected from the group consisting of sodium monochloroacetic acid, potassium monochloroacetic acid, and lithium monochloroacetic acid. The molar ratio of the alkali metal salt of monochloroacetic acid to alkali metal bicarbonate is in the range of 1.3:1.1 to 1.3:1.5.

In the second step, 4-(methylsulfonyl) toluene is nitrated using a mixture of sulphuric acid and at least one nitrating agent to obtain 2-nitro-4-methylsulfonyl toluene.

The nitrating agent is at least one selected from the group consisting of nitric acid, potassium nitrate, and sodium nitrate. In one embodiment of the present disclosure, the nitration is carried out using mixed acid comprising oleum (24%) and nitric acid.

In the third step, 2-nitro-4-methylsulfonyl toluene is oxidized using at least one oxidizing agent in the presence of at least one first catalyst to obtain 2-nitro-4-methylsulfonylbenzoic acid.

The oxidizing agent is at least one selected from the group consisting of sulphuric acid, hydrogen peroxide, sodium hypochlorite, nitric acid and air-Co—Mn catalyst. The first catalyst is vanadium pentoxide.

In the fourth step, 2-nitro-4-methylsulfonylbenzoic acid is halogenated using at least one halogenating agent in a first fluid medium to obtain 2-nitro-4-methylsulfonylbenzoyl halide.

In one embodiment of the present disclosure, the halogenating agent is thionyl chloride. The first fluid medium is at least one selected from the group consisting of ethylene dichloride and methylene dichloride. In an embodiment, dimethylformamide was added during the step of halogenation.

In the fifth step, 2-nitro-4-methylsulfonylbenzoyl halide is reacted with alkali metal salt of 1,3-cyclohexanedione at a temperature in the range of 0° C. to 15° C. in the presence of a second fluid medium, and at least one second catalyst to obtain 3-(2-Nitro-4-methyl sulfonylbenzoyloxy)cyclohexen-1-one.

The second fluid medium is ethylene dichloride.

The second catalyst is at least one selected from the group consisting of tetrabutylammonium bromide, tetramethyl ammonium chloride, triethylbenzyl ammonium chloride, and triphenyl phosphonium bromide.

In the sixth step, 3-(2-Nitro-4-methylsulfonylbenzoyloxy)cyclohexen-1-one is reacted with at least one base, a third fluid medium and at least one cyanide ion source to obtain an amorphous mesotrione having purity less than or equal to 99%.

The third fluid medium is ethylene dichloride.

The base is at least one selected from the group consisting of triethylamine, sodium hydride, and 1,2,4-triazole.

The cyanide ion source is at least one selected from the group consisting of acetone cyanohydrin, sodium cyanide, potassium cyanide, and hydrogen cyanide.

In the seventh step, the amorphous mesotrione is converted to the crystalline mesotrione having purity greater than 99%.

The present disclosure further discloses the process for the conversion of amorphous mesotrione to crystalline mesotrione.

BRIEF DESCRIPTION OF ACCOMPANYING DRAWING

Figure 2:
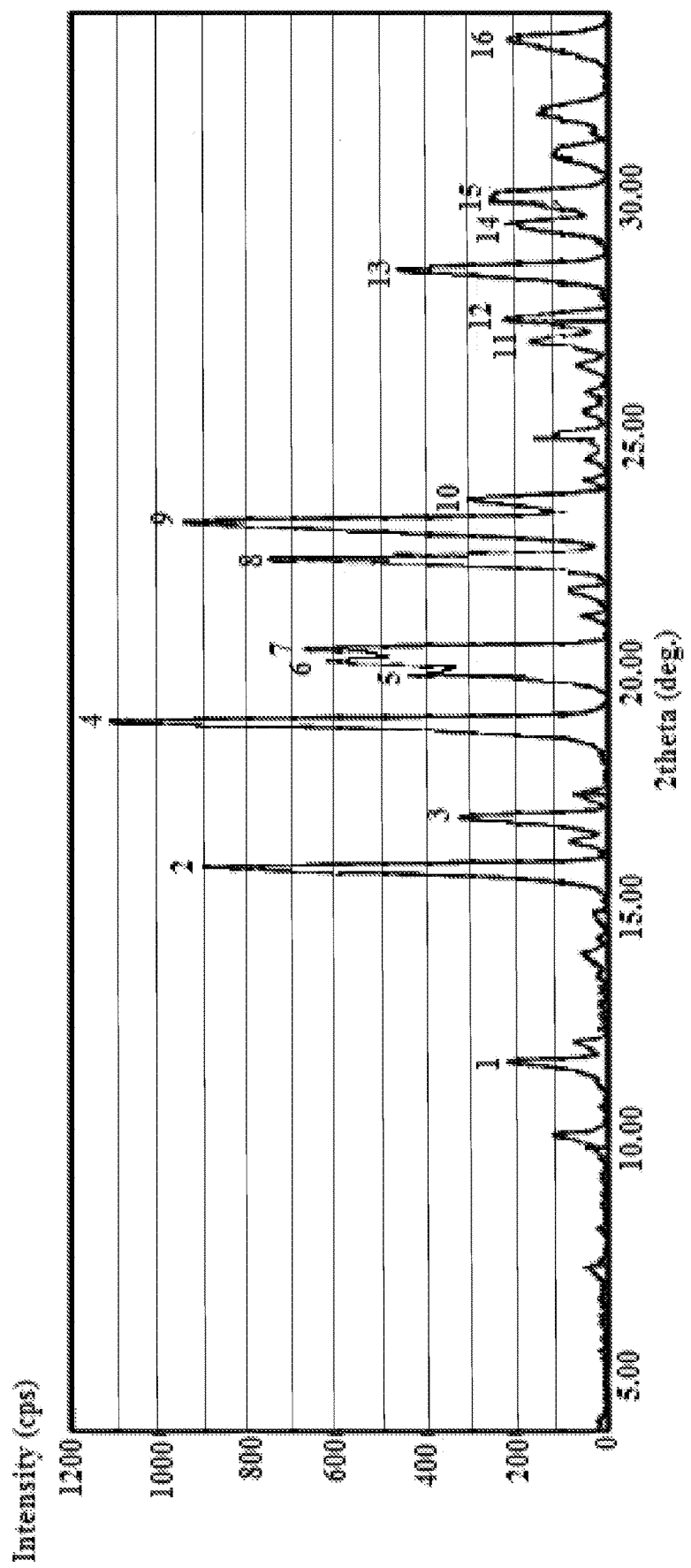

The process of synthesis of mesotrione of the present disclosure will now be described with the help of the accompanying drawing, in which:

FIG. 1 illustrates the XRD (X-ray diffractogram) peaks of crystalline mesotrione prepared in accordance with the present disclosure; and FIG. 2 illustrates the XRD peaks of metastable form of mesotrione prepared in accordance with the present disclosure.

DETAILED DESCRIPTION

Embodiments, of the present disclosure, will now be described with reference to the accompanying drawing.

Embodiments are provided so as to thoroughly and fully convey the scope of the present disclosure to the person skilled in the art. Numerous details are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise. The terms "comprises," "comprising," "including," and "having," are open ended transitional phrases and therefore specify the presence of stated features, integers, steps, operations, elements, modules, units and/or components, but do not forbid the presence or addition of one or more other features, integers, steps, operations, elements, components, and/or groups thereof. The particular order of steps disclosed in the method and process of the present disclosure is not to be construed as necessarily requiring their performance as described or illustrated. It is also to be understood that additional or alternative steps may be employed.

The terms first, second, third, etc., should not be construed to limit the scope of the present disclosure as the aforementioned terms may be only used to distinguish one element, component, region, layer or section from another component, region, layer or section. Terms such as first, second, third etc., when used herein do not imply a specific sequence or order unless clearly suggested by the present disclosure.

The present disclosure envisages a rapid, efficient, economical, and environment friendly process for the synthesis of crystalline mesotrione that mitigates the drawbacks mentioned herein above.

In accordance with the present disclosure the process for the synthesis of crystalline mesotrione comprises the following steps:

i. 4-toluenesulfonyl chloride is reacted with at least one alkali metal sulphite and at least one alkali metal bicarbonate, to obtain alkali metal toluene-4-sulfinate, followed by reacting alkali metal toluene-4-sulfinate with at least one alkali metal salt of monochloroacetic acid to obtain 4-methylsulfonyl toluene;

ii. 4-(methylsulfonyl) toluene is nitrated using a mixture of sulphuric acid and at least one nitrating agent to obtain 2-nitro-4-methylsulfonyl toluene;

iii. 2-nitro-4-methylsulfonyl toluene is oxidized using at least one oxidizing agent in the presence of at least one first catalyst to obtain 2-nitro-4-methylsulfonylbenzoic acid;

iv. 2-nitro-4-methylsulfonylbenzoic acid is halogenated using at least one halogenating agent in a first fluid medium to obtain 2-nitro-4-methylsulfonylbenzoyl halide;

v. 2-nitro-4-methylsulfonylbenzoyl halide is reacted with alkali metal salt of 1,3-cyclohexanedione at a temperature in the range of 0° C. to 15° C. in the presence of a second fluid medium, and at least one second catalyst to obtain 3-(2-Nitro-4-methyl sulfonylbenzoyloxy)cyclohexen-1-one;

vi. 3-(2-Nitro-4-methylsulfonylbenzoyloxy)cyclohexen-1-one is reacted with at least one base, a third fluid medium and at least one cyanide ion source to obtain an amorphous mesotrione having purity less than or equal to 99%; and vii. The amorphous mesotrione is converted to the crystalline mesotrione having purity greater than 99%.

The steps used in the process for the synthesis of mesotrione are described in detail as follows:

First Step: Synthesis of 4-methylsulfonyl toluene from 4-toluenesulfonyl chloride In the first step, 4-toluene sulfonyl chloride is reacted with at least one alkali metal sulphite selected from the group consisting of sodium sulphite, potassium sulphite and lithium sulphite; and at least one alkali metal bicarbonate, such as sodium bicarbonate, potassium bicarbonate, and lithium bicarbonate, under stirring to obtain a mass comprising alkali metal toluene-4-sulfinate. The molar ratio of 4-toluenesulfonyl chloride:alkali metal sulphite:alkali metal bicarbonate is in the range of 1:1:2 to 1:1.5:2.5. In an exemplary embodiment, the molar ratio of 4-toluenesulfonyl chloride to alkali metal sulphite to alkali metal bicarbonate is 1:1.2:2.2.

The schematic representation for the synthesis of 4-methylsulfonyl toluene in an embodiment of the present disclosure is shown below:

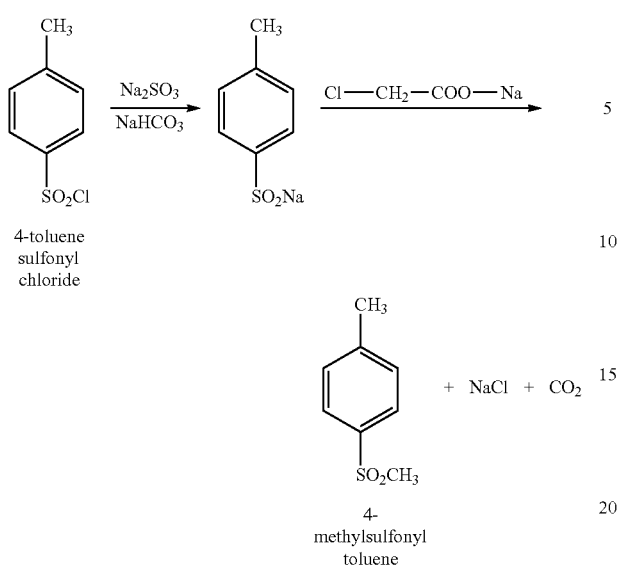

4-toluene sulfonyl chloride 4-methylsulfonyl toluene

Typically, sodium sulphite and sodium bicarbonate along with water are charged into a reactor under stirring, to get a clear solution. The clear solution is heated at a temperature in the range of 65° C. to 85° C., followed by the slow addition of 4-toluene sulfonyl chloride over a period in the range of 6 hours to 10 hours, and further stirred for a time period in the range of 1 hour to 2 hours to obtain a mass comprising sodium toluene-4-sulfinate.

The mass comprising sodium toluene-4-sulfinate is cooled under stirring, and reacted with at least one alkali metal salt of monochloroacetic acid solution, such as sodium monochloroacetic acid, potassium monochloroacetic acid, and lithium monochloroacetic acid, preferably under pressure and stirring, to obtain a mass comprising 4-methylsulfonyl toluene.

In accordance with an embodiment of the present disclosure, the alkali metal salt of monochloroacetic acid solution is prepared by adding monochloroacetic acid into water, followed by slow addition of alkali metal bicarbonate over a time period in the range of 1 hour to 2 hours under stirring. The ratio of monochloroacetic acid to alkali metal bicarbonate is in the range of 1.3:1.1 to 1.3:1.5. In an exemplary embodiment, the ratio of monochloroacetic acid to alkali metal bicarbonate is 1.3:1.18.

Typically, the mass comprising sodium toluene-4-sulfinate is cooled to a temperature in the range of 35° C. to 55° C., followed by the addition of the sodium salt of monochloroacetic acid solution over a period in the range of 2 hours to 3 hours under continuous stirring to obtain a reaction mixture. The reaction mixture is then transferred into stainless steel pressure reactor. The temperature of the stainless steel pressure reactor is raised in the range of 100° C. to 120° C. at a pressure in the range of 3 kg/cm² to 7 kg/cm², followed by maintaining the reaction mixture at a temperature in the range of 130° C. to 150° C. to obtain a mass comprising 4-methylsulfonyl toluene. The so obtained mass comprising 4-methylsulfonyl toluene is worked up using known techniques to obtain 4-methylsulfonyl toluene having purity of at least 95%.

Carbon dioxide is evolved during the synthesis of 4-methylsulfonyl toluene from alkali metal toluene-4-sulfinate, and is scrubbed into alkali metal hydroxide to get the respective alkali metal bicarbonate, which is reused for the next reaction and thereby, reducing the effluent and hence the environmental load.

Second Step: Synthesis of 2-nitro-4-methylsulfonyl toluene from 4-methylsulfonyl toluene In the second step, the so obtained 4-methylsulfonyl toluene is subjected to nitration using a mixture of 95% to 98% of $H_2SO_4$ and at least one nitrating agent, such as nitric acid ($HNO_3$), potassium nitrate ($KNO_3$), and sodium nitrate ($NaNO_3$) to obtain a mass comprising 2-nitro-4-methylsulfonyl toluene.

In one embodiment, the nitration is carried out by using a mixed acid comprising 24% of oleum and nitric acid. Oleum (fuming sulphuric acid) is a solution of various compositions of sulfur trioxide in sulphuric acid. Oleum can be described by the formula $ySO_3.H_2O$ where y is the total molar sulfur trioxide content or by the formula $H_2SO_4.xSO_3$ where x is now defined as the molar free sulfur trioxide content. Oleum is generally assessed according to the free $SO_3$ content by mass. It can also be expressed as a percentage of sulphuric acid strength.

The schematic representation of the synthesis of 2-nitro-4-methylsulfonyl toluene in accordance with an embodiment of the present disclosure is shown below:

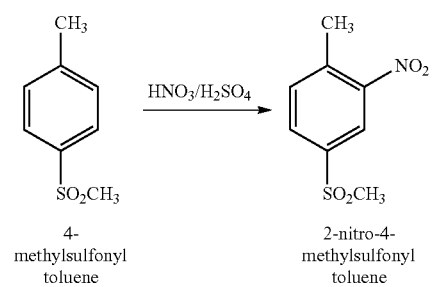

4-methylsulfonyl toluene 2-nitro-4-methylsulfonyl toluene

Typically, 4-methylsulfonyl toluene is reacted with sulphuric acid under stirring (prior to nitration), followed by slow addition of the mixed acid at a temperature in the range of 8° C. to 30° C., for a time period in the range of 2 hours to 5 hours under stirring, to obtain 2-nitro-4-methylsulfonyl toluene. The so obtained mass comprising 2-nitro-4-methylsulfonyl toluene is worked up using known techniques to obtain 2-nitro-4-methylsulfonyl toluene having purity of at least 95%.

Third Step: Synthesis of 2-nitro-4-methylsulfonylbenzoic acid from 2-nitro-4-methylsulfonyl toluene The schematic representation of the synthesis of 2-nitro-4-methylsulfonylbenzoic acid is as shown below:

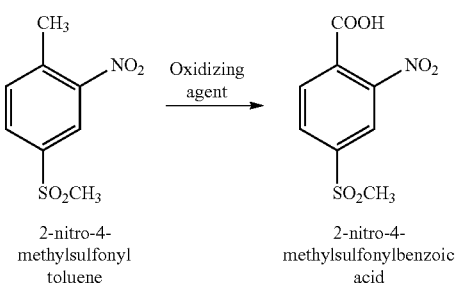 [SMILES: Cc1ccc(S(C)(=O)=O)cc1[N+](=O)[O-] ; "Oxidizingagent" ; CS(=O)(=O)c1ccc(C(=O)O)c([N+](=O)[O-])c1]

2-nitro-4-methylsulfonyl toluene → 2-nitro-4-methylsulfonylbenzoic acid

In the third step, the so obtained 2-nitro-4-methylsulfonyl toluene is oxidized using at least one oxidizing agent in the presence of a first catalyst at a temperature in the range of 130° C. to 170° C. for a time period in the range of 6 hours to 10 hours, to obtain a mass comprising 2-nitro-4-methylsulfonylbenzoic acid. The mass comprising 2-nitro-4-methylsulfonyl benzoic acid is worked up using known techniques to obtain 2-nitro-4-methylsulfonyl benzoic acid having purity of at least 95%.

In an exemplary embodiment of the present disclosure, the first catalyst is vanadium pentoxide.

Typically, the oxidizing agent is selected from the group consisting of sulphuric acid ($H_2SO_4$), hydrogen peroxide ($H_2O_2$), sodium hypochlorite, nitric acid ($HNO_3$) and air-Co—Mn catalyst.

In one embodiment, 70% to 75% $H_2SO_4$ along with air is used as the oxidizing agent. In another embodiment, 10% to 20% of $HNO_3$ along with air, is used as the oxidizing agent, at a temperature in the range of 160° C. to 180° C.

$HNO_3$ is slowly added over a period in the range of 6 hours to 10 hours along with the passing of the required air with scrubbing off gases into dilute sodium hydroxide (NaOH) and dilute ammonia solution. After the completion of the reaction, $HNO_3$ used during the oxidation step is recovered from the reaction mixture ($HNO_3$ Recovered=4.5-5.0 M/M i.e., $HNO_3$ consumed=4.5-5.0 M/M).

Typically, the 70% to 75% $H_2SO_4$ used in the oxidation step is the diluted $H_2SO_4$ which is the recovered from the concentrated $H_2SO_4$ used in the nitration of 4-methylsulfonyl toluene. Reuse of $H_2SO_4$ results in an economical process and thus also reduces the amount of the effluent produced and is therefore environment friendly.

The concentrated $H_2SO_4$, i.e., 98% $H_2SO_4$ used in the nitration reaction gets diluted during the reaction process. The diluted sulphuric acid obtained, is concentrated to get sulphuric acid of 70% concentration. The 70% sulphuric acid is recycled again for the next batch without addition of fresh catalyst (vanadium pentoxide) into the reaction. This avoids the generation of effluent and saves the catalyst quantity as the same catalyst can be reused for the next batch which makes the reaction of the present disclosure economical and environment friendly.

Fourth Step: Synthesis of
2-nitro-4-methylsulfonylbenzoyl halide from
2-nitro-4-methylsulfonylbenzoic acid In the fourth step, the so obtained 2-nitro-4-methylsulfonylbenzoic acid is halogenated using at least one halogenating agent, in a first fluid medium to obtain 2-nitro-4-methylsulfonylbenzoyl halide. In an exemplary embodiment, the halogenation is carried out using a chlorinating agent.

In one embodiment, the chlorinating agent is thionyl chloride ($SOCl_2$).

In accordance with the embodiments of the present disclosure, the first fluid medium is selected from ethylene dichloride (EDC), and methylene dichloride (MDC).

The schematic representation of the synthesis of 2-nitro-4-methylsulfonylbenzoyl chloride in accordance with an embodiment of the present disclosure is shown below:

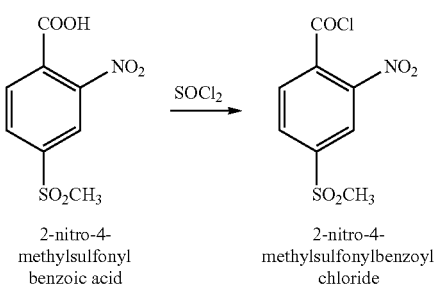

2-nitro-4-methylsulfonyl benzoic acid → 2-nitro-4-methylsulfonylbenzoyl chloride Typically, 2-nitro-4-methylsulfonylbenzoic acid, dimethylformamide, and ethylene dichloride can be mixed to obtain a mixture. At least one chlorinating agent can be added to the so obtained mixture at a temperature in the range of 20° C. to 40° C. over a period in the range of 15 minutes to 60 minutes, followed by heating at a temperature in the range of 70° C. to 90° C. for a time period in the range of 3 hours to 5 hours, to obtain a reaction mass. The process is carried out under continuous stirring.

During work up of the so obtained reaction mass, the chlorinating agent is distilled out, at a temperature in the range of 65° C. to 70° C., followed by repetitive addition and distillation of ethylene dichloride along with chlorinating agent to obtain a cake. The so obtained cake is washed with ethylene dichloride and dried to obtain 2-nitro-4-methylsulfonylbenzoyl chloride.

In accordance with an embodiment of the present disclosure, the so obtained 2-nitro-4-methylsulfonylbenzoyl chloride has a purity of at least 95%.

Additional/Optional Step: Synthesis of Alkali Metal
Salt of 1,3-cyclohexanedione from
1,3-dihydroxybenzene Separately, 1,3-dihydroxybenzene is reduced using reducing agent, and an alkaline hydroxide solution, preferably in the presence of at least one hydrogenating catalyst, to obtain alkali metal salt of 1,3-cyclohexanedione.

The schematic representation of the reaction is as shown below:

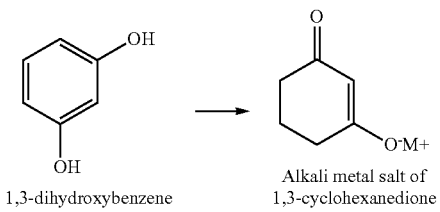

1,3-dihydroxybenzene → Alkali metal salt of 1,3-cyclohexanedione wherein M+ is alkali metal.

In accordance with an embodiment of the present disclosure, the alkaline hydroxide is selected from sodium hydroxide and potassium hydroxide. In an exemplary embodiment the ratio of 1,3-dihydroxybenzene to alkaline hydroxide solution is 1:1.033.

In an exemplary embodiment of the present disclosure, the hydrogenating catalyst is Raney nickel and the reducing agent is hydrogen.

Typically, the reaction can be carried out by charging 1,3-dihydroxybenzene, water, sodium hydroxide (NaOH), Raney nickel, into a reactor, at a pressure in the range of 3 kg to 8 kg with hydrogen and at a temperature in the range of 50° C. to 90° C. Further, the reaction is maintained by subjecting to a pressure in the range of 10 kg to 20 kg with hydrogen to obtain a mass comprising sodium salt of 1,3-cyclohexanedione. The reaction is monitored by using HPLC till no consumption of $H_2$ is observed in the sample.

The mass comprising sodium salt of 1,3-cyclohexanedione is worked up using known techniques to obtain sodium salt of 1,3-cyclohexanedione having purity of at least 97%.

Fifth step: Synthesis of 3-(2-Nitro-4-methylsulfonylbenzoyloxy)cyclohexen-1-one

In the fifth step, a second fluid medium, 2-nitro-4-methylsulfonylbenzoyl halide and at least one second catalyst are charged into a reactor, to obtain a mass. The mass is cooled to a temperature in the range of 0° C. to 15° C., followed by the addition of alkali salt of 1,3-cyclohexanedione at a temperature in the range of 0° C. to 15° C. over a time period in the range of 1 hour to 2 hours and then maintained at a temperature in the range of 0° C. to 15° C. for a time period in the range of 2 hours to 6 hours, to obtain a mass comprising 3-(2-Nitro-4-methyl sulfonylbenzoyloxy)cyclohexen-1-one.

Since benzoyl halides are unstable at higher temperatures in the presence of moisture the synthesis of 3-(2-Nitro-4-methylsulfonylbenzoyloxy)cyclohexen-1-one from 2-nitro-4-methylsulfonylbenzoyl halide is carried out at a temperature in the range of 0° C. to 15° C.

In an exemplary embodiment of the present disclosure, the second fluid medium is ethylene dichloride.

In accordance with an embodiment of the present disclosure, the second catalyst is a quaternary ammonium salt selected from the group consisting of tetrabutylammonium bromide, tetramethyl ammonium chloride, triethylbenzyl ammonium chloride, and triphenyl phosphonium bromide.

The schematic representation of the synthesis of 3-(2-Nitro-4-methylsulfonylbenzoyloxy)cyclohexen-1-one in accordance with an embodiment of the present disclosure is shown below:

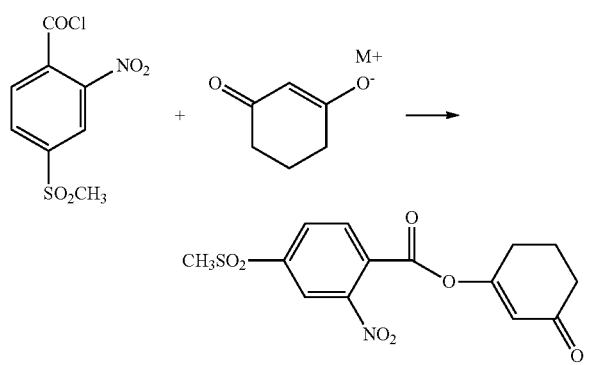

The mass comprising 3-(2-Nitro-4-methylsulfonylbenzoyloxy)cyclohexen-1-one is worked up using known techniques to obtain 3-(2-Nitro-4-methylsulfonylbenzoyloxy)cyclohexen-1-one having purity of at least 95%.

Sixth Step: Synthesis of Mesotrione from 3-(2-Nitro-4-methylsulfonylbenzoyloxy)cyclohexen-1-one The schematic representation of the synthesis of mesotrione is as shown below:

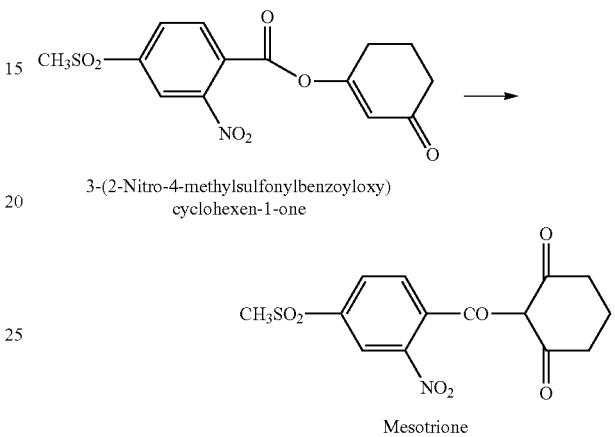

In the sixth step, 3-(2-Nitro-4-methylsulfonylbenzoyloxy)cyclohexen-1-one is mixed with a third fluid medium followed by the addition of at least one base at a temperature in the range of 20° C. to 40° C. for a time period in the range of 10 minutes to 20 minutes to obtain a thin slurry. At least one source of cyanide ion is added to the thin slurry and stirred at a temperature in the range of 20° C. to 40° C. for a time period in the range of 2 hours to 4 hours to obtain a reaction mass comprising amorphous mesotrione.

The source of cyanide ion is at least one selected from the group consisting of acetone cyanohydrin, sodium cyanide, potassium cyanide, and hydrogen cyanide.

Typically, the base is selected from the group consisting of triethylamine, sodium hydride, and 1,2,4-triazole. In accordance with an exemplary embodiment of the present disclosure, the base is triethylamine and the third fluid medium is ethylene dichloride.

The mass comprising mesotrione is worked up using known techniques to obtain mesotrione having purity less than or equal to 99%.

Seventh Step: Conversion of Amorphous Mesotrione to Crystalline Mesotrione

Method 1

The amorphous mesotrione is solubilized using a fourth fluid medium to obtain a solution. In an exemplary embodiment of the present disclosure, the fourth fluid medium is ethylene dichloride. The solution is then treated with charcoal to obtain a first mixture. A portion of the fourth fluid medium is distilled out from the first mixture to obtain a second mixture comprising a remaining portion of the fourth fluid medium, and crystalline mesotrione. The second mixture is then filtered to obtain a first residue comprising the crystalline mesotrione and a first filtrate comprising the remaining portion of the fourth fluid medium and residue mesotrione. The first residue is dried to obtain a first portion of crystalline mesotrione. The HPLC purity of the first portion of crystalline mesotrione is greater than 99%.

The first filtrate is then treated with an aqueous alkali solution to obtain a biphasic mixture comprising aqueous layer comprising metastable form of mesotrione and an organic layer comprising the fourth fluid medium. The aqueous alkali solution is at least one selected from the group consisting of triethylamine, sodium hydroxide, and potassium hydroxide.

The aqueous layer is separated from the organic layer.

The aqueous layer is then acidified with an acid to obtain an acidified aqueous layer having a pH below 0.8. The acidified aqueous layer is filtered to obtain an metastable form of mesotrione. The pH of the aqueous layer is maintained below 0.8 to obtain the desired form of mesotrione i.e., metastable form of mesotrione. If pH of the aqueous layer is maintained above 0.8 then the mesotrione obtained is of different form which is undesirable. The acid is selected from the group consisting of citric acid, hydrochloric acid and sulphuric acid.

The process of obtaining the first residue as stated above is reiterated to convert the metastable form of mesotrione to crystalline mesotrione.

The yield of the crystalline mesotrione is greater than 96%.

Method 2

The process for converting amorphous mesotrione to crystalline mesotrione is similar to the process as disclosed in Method 1, except the first filtrate obtained in the Method 1 is evaporated to obtain a remaining portion of mesotrione.

The HPLC purity of the crystalline mesotrione obtained by using either method 1 or method 2 is greater than 99%.

Overall, the process of the present disclosure for the synthesis of mesotrione is rapid, economical, and environment friendly. The process of the present disclosure produces mesotrione with high yield and high purity.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

The present disclosure is further described in light of the following laboratory scale experiments which are set forth for illustration purpose only and not to be construed for limiting the scope of the disclosure. These laboratory scale experiments can be scaled up to industrial/commercial scale and the results obtained can be extrapolated to industrial/commercial scale.

EXPERIMENTAL DETAILS

Experiment 1: Synthesis of Mesotrione

Step 1: Synthesis of 4-methylsulfonyl toluene 151 g of sodium sulfite and 185 g of sodium bicarbonate were dissolved in 500 ml of water and heated to 75° C. to obtain a solution. 4-toluenesulfonyl chloride (190.5 g) was added to the so obtained solution over a period of 9 hours at 75° C. to obtain a reaction mixture. The so obtained reaction mixture was cooled to 45° C. and a clear solution of sodium salt of monochloroacetic acid was added over an hour and further stirred for 30 minutes to obtain a cooled reaction mixture. The sodium salt of monochloroacetic acid was prepared from 122 g of monochloroacetic acid in 300 ml of water and addition of 100 g of sodium bicarbonate. The so obtained cooled reaction mixture was heated to 120° C. at a pressure of 5 kg/cm² for 5 hours, followed by heating at 130° C. for 4 hours under pressure of 5 kg/cm² to obtain a product mixture. The product mixture was slowly cooled to 10° C. to yield 162 g of 4-methylsulfonyl toluene having HPLC purity of 99.44%.

Step 2: Synthesis of 2-nitro-4-methylsulfonyl toluene 170 g of 4-methylsulfonyl toluene obtained in step 1 was added in 100 g of sulphuric acid (98%) and stirred at room temperature for 30 minutes and then cooled to 10° C. to obtain a reaction mixture. A mixture of 100 g of oleum (24%) and 70 g of nitric acid (98%) was added over 4 hours at 10° C. to the reaction mixture to obtain a resultant mixture. The resultant mixture was stirred for 6 hours to obtain a reaction mass. The reaction mass was drowned into ice water, stirred, and filtered to obtain a cake containing 2-nitro-4-methylsulfonyl toluene. The so obtained cake was washed with water and dried in an oven at 80° C. to obtain 205 g of 2-nitro-4-methylsulfonyl toluene having HPLC purity of 99.38%.

Step 3: Synthesis of 2-nitro-4-methylsulfonylbenzoic acid 215 g of 2-Nitro-4-methylsulfonyl toluene obtained in step 2, and 3 g of vanadium pentoxide were dissolved in 1500 ml of sulphuric acid (70%) to obtain a reaction mixture. The reaction mixture was heated to 145° C. with air passing, followed by adding 430 ml of nitric acid (65%) over a period of 8 hours to obtain a reaction mass. The reaction mass was stirred for 2 hours at 145° C. The reaction mass was further stirred at 165° C. for 3 hours, and cooled to obtain a cooled reaction mass. The cooled reaction mass was drowned into ice water, stirred, and filtered to obtain a cake containing 2-nitro-4-methylsulfonylbenzoic acid. The so obtained cake was washed with water and dried in an oven at 80° C. to obtain 160 g of 2-nitro-4-methylsulfonylbenzoic acid having HPLC purity of 99%.

Step 4: Synthesis of 2-nitro-4-methylsulfonylbenzoyl chloride 245 g of 2-nitro-4-methylsulfonylbenzoic acid obtained step 3, and 2 ml of dimethylformamide were mixed to obtain a mixture. The so obtained mixture was added to 500 ml of ethylene dichloride and stirred for 30 minutes to obtain a reaction mixture. 238 g of thionyl chloride was added to the reaction mixture at 30° C. over 30 minutes to obtain a reaction mass. The so obtained reaction mass was heated to 80° C. for 4 hours. Thionyl chloride was distilled out at 65° C. from the reaction mass. 250 ml of ethylene dichloride was added to the reaction mass and the reaction mass was stirred for 1 hour. Further, ethylene dichloride and thionyl chloride were distilled out. Further, 100 ml of ethylene dichloride was added to the reaction mass and cooled to 10° C. to obtain a cooled reaction mass. The so obtained cooled reaction mass was filtered to obtain a cake. The cake was washed with ethylene dichloride and dried to yield 242 g of 2-nitro-4-methylsulfonylbenzoyl chloride having the HPLC purity of 98%.

Synthesis of Sodium Salt of 1,3-cyclohexanedione 110 gm of 1,3-dihydroxybenzene in 1M sodium hydroxide solution was hydrogenated in the presence of Raney Nickel catalyst at a pressure of 10 kg/cm$^2$ at 70° C. for 6 hours to obtain a reaction mass. The 1M sodium hydroxide solution was prepared by dissolving 40 g of sodium hydroxide in 300 ml of water. The reaction mass was allowed to settle for 1 hour and a clear mass containing 450 g of sodium salt of 1,3-cyclohexanedione (95% yield) was decanted keeping the catalyst inside the reactor for next batch.

Step 5: Synthesis of 3-(2-Nitro-4-methylsulfonylbenzoyloxy)cyclohexen-1-one

Method A:

263.5 g of 2-nitro-4-methylsulfonylbenzoyl chloride obtained in step 4, 3.30 g of tetrabutylammonium bromide and 1000 ml of ethylene dichloride were charged into a reactor to obtain a reaction mass. The reaction mass was cooled to 10° C. to obtain a cooled reaction mass followed by adding sodium salt of 1,3-cyclohexanedione (515 g) at 10° C. over a period of 1.5 hours. The cooled reaction mass was maintained at 10° C. for 4 hours. The reaction mass was further cooled to 5° C., filtered, and washed with ethylene dichloride. The mass obtained was vacuum dried to yield 318 g of 3-(2-Nitro-4-methylsulfonylbenzoyloxy)cyclohexen-1-one (92%) having HPLC purity of 98%.

Method B:

263.5 g of 2-nitro-4-methylsulfonylbenzoyl chloride obtained in step 4, 3.30 g of tetrabutylammonium bromide and 1200 ml of ethylene dichloride were charged into a reactor to obtain a reaction mass. The reaction mass was cooled to 2° C. to obtain a cooled reaction mass followed by adding 1,3-cyclohexanedione sodium salt aq. solution (518 g, 28% aq. solution) at 2° C. over a period of 2 hours. The cooled reaction mass was maintained at 2° C. for 4 hours. The reaction mass was further cooled to 0° C., filtered, and washed with ethylene dichloride. The mass obtained was vacuum dried to yield 322 g of 3-(2-Nitro-4-methylsulfonylbenzoyloxy)cyclohexen-1-one (94%) having HPLC purity of 99%.

Method C:

263.5 g of 2-nitro-4-methylsulfonylbenzoyl chloride obtained step 4, 3.30 g of tetrabutylammonium bromide and 1000 ml of ethylene dichloride were charged into a reactor to obtain a reaction mass. The reaction mass was cooled to 5° C. to obtain a cooled reaction mass followed by adding 1,3-cyclohexanedione sodium salt aq. solution (518 g, 28% aq. solution) at 5° C. over a period of 2 hours. The cooled reaction mass was maintained at 5° C. for 4 hours. The reaction mass was further cooled to 0° C., filtered, and washed with ethylene dichloride. The mass obtained was vacuum dried to yield 320 g of 3-(2-Nitro-4-methylsulfonylbenzoyloxy)cyclohexen-1-one (93%) having HPLC purity of 98.5%.

Step 6: Synthesis of 2-[4-(methanesulfonyl)-2-nitrobenzoyl]cyclohexane-1,3-dione (mesotrione)

1100 ml of ethylene dichloride and 346 g of 3-(2-Nitro-4-methylsulfonylbenzoyloxy)cyclohexen-1-one (98%) obtained in step 5 were charged in a reactor. 121 g of triethylamine was added to the mixture and the mixture was heated at 30° C. for 15 minutes to make a slurry. 8.5 g of acetone cyanohydrin was added to the slurry and stirred at 30° C. for 3 hours to obtain a reaction mass. The reaction mass was diluted with 300 ml of ethylene dichloride and further drowned in 2000 ml of water at 20° C. Aqueous layer was separated and worked up to isolate 305 g of amorphous mesotrione having HPLC purity of 99%.

Purification of Mesotrione: Converting Amorphous Mesotrione to Crystalline Mesotrione Method 1:

The amorphous mesotrione (1350 g) was solubilized in ethylene dichloride (16.2 L) to obtain a solution. The so obtained solution was treated with charcoal (19.89 g) to obtain a first mixture. A portion of the ethylene dichloride (14.1 L) was distilled out from the first mixture at 30° C. and at a pressure of 70 mmHg to obtain a second mixture comprising a remaining portion of the ethylene dichloride (2.7 L), and crystalline mesotrione. The second mixture was filtered to obtain a first residue comprising the crystalline mesotrione and a first filtrate comprising the remaining portion of the ethylene dichloride and residue mesotrione. The first residue was dried to obtain a first portion of crystalline mesotrione (Crop-I). The HPLC purity of the first portion of crystalline mesotrione was found to be 99.984%. The yield of the first portion of the crystalline mesotrione was found to be 1190 g.

The crystalline mesotrione prepared in accordance with the present disclosure was characterized by X-ray diffraction. The XRD data obtained for the mesotrione of the present disclosure confirms the formation of crystalline mesotrione as shown in FIG. 1.

Further, the first filtrate was treated with sodium hydroxide solution (135 ml) to obtain a biphasic mixture comprising aqueous layer comprising the metastable form of mesotrione and an organic layer comprising the remaining portion of the ethylene dichloride. The aqueous layer was separated from the organic layer. The separated aqueous layer was acidified with hydrochloric acid to obtain an acidified aqueous layer having a pH of 0.8. The acidified aqueous layer was filtered to obtain the metastable form of mesotrione (Crop-II). The metastable form of mesotrione obtained by the process of the present disclosure was characterized by X-ray diffraction. The XRD data obtained for the so formed mesotrione confirms the formation of metastable form of mesotrione as shown in FIG. 2. The HPLC purity of the metastable form of mesotrione was found to be 99.906%. The yield of the metastable form of mesotrione was found to be 116 g.

The so obtained metastable form of mesotrione was further processed by reiterating the steps of method 1 of the present disclosure to convert the metastable form of mesotrione to crystalline mesotrione.

The total yield of the crystalline mesotrione was found to be 96.74%.

Method 2:

The amorphous mesotrione (1373 g) was solubilized in ethylene dichloride (16.4 L) to obtain a solution. The so obtained solution was treated with charcoal (20.2 g) to obtain a first mixture. A portion of the ethylene dichloride (14.2 L) was distilled out from the first mixture at 30° C. and at a pressure of 70 mmHg to obtain a second mixture comprising a remaining portion of the ethylene dichloride (2.8 L), and crystalline mesotrione. The second mixture was filtered to obtain a first residue comprising the crystalline mesotrione and a first filtrate comprising the remaining portion of the ethylene dichloride. The first residue was dried to obtain a first portion of crystalline mesotrione (Crop-I). The HPLC purity of the first portion of crystalline mesotrione was found to be 99.9%. The yield of the first portion of the crystalline mesotrione was found to be 1244 g.

Further, the first filtrate was evaporated to dryness to obtain a remaining portion of mesotrione (Crop-II). The yield of the remaining mesotrione was found to be 101 g.

The total yield of crystalline mesotrione was found to be 97.96%.

It is evident from the above reaction steps that the process of the present disclosure employs mild reaction conditions, employs readily available reagents that are cheap and reduce the release of environmentally hazardous effluents. Also, the process of the present disclosure produces mesotrione with high yield and high purity. Therefore, the process of the present disclosure to synthesize mesotrione is rapid, economic, and environment friendly. The mesotrione produced by the process of the present disclosure has high yield and high purity.

Technical Advances and Economical Significance

The present disclosure described herein above has several technical advantages including, but not limited to, the realization of a process for the synthesis of mesotrione:

that is rapid, economic, and environment friendly; and with high yield and high purity.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results. While certain embodiments of the inventions have been described, these embodiments have been presented by way of experiment only, and are not intended to limit the scope of the inventions. Variations or modifications to the formulation of this invention, within the scope of the invention, may occur to those skilled in the art upon reviewing the disclosure herein. Such variations or modifications are well within the spirit of this invention.

The numerical values given for various physical parameters, dimensions, and quantities are only approximate values and it is envisaged that the values higher than the numerical value assigned to the physical parameters, dimensions and quantities fall within the scope of the invention unless there is a statement in the specification to the contrary.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A process for synthesis of crystalline mesotrione, said process comprising the following steps:
   i. reacting 4-toluenesulfonyl chloride with at least one alkali metal sulphite and at least one alkali metal bicarbonate, to obtain alkali metal toluene-4-sulfinate, followed by reacting said alkali metal toluene-4-sulfinate with at least one alkali metal salt of monochloroacetic acid to obtain 4-methylsulfonyl toluene;
   ii. nitrating 4-methylsulfonyl toluene using sulphuric acid followed by a mixture of nitric acid and oleum to obtain 2-nitro-4-methylsulfonyl toluene;
   iii. oxidizing 2-nitro-4-methylsulfonyl toluene using at least one oxidizing agent in the presence of at least one first catalyst to obtain 2-nitro-4-methylsulfonylbenzoic acid;
   iv. halogenating 2-nitro-4-methylsulfonylbenzoic acid using at least one halogenating agent in a first fluid medium to obtain 2-nitro-4-methylsulfonylbenzoyl halide;
   v. reacting 2-nitro-4-methylsulfonylbenzoyl halide with aqueous solution of alkali metal salt of 1,3-cyclohexanedione in a two phase system at a temperature in the range of 0° C. to 15° C. in the presence of a second fluid medium, and at least one second catalyst to obtain 3-(2-Nitro-4-methylsulfonylbenzoyloxy)cyclohexen-1-one;
   vi. reacting 3-(2-Nitro-4-methylsulfonylbenzoyloxy)cyclohexen-1-one with at least one base, a third fluid medium and at least one cyanide ion source to obtain an amorphous mesotrione with yield of 87.7% or greater and having purity less than or equal to 99%; and
   vii. converting said amorphous mesotrione to said crystalline mesotrione having purity greater than 99%.

2. The process as claimed in claim 1, wherein said step (vii) of converting said amorphous mesotrione to said crystalline mesotrione comprises:
   a. solubilizing said amorphous mesotrione using a fourth fluid medium to obtain a solution;
   b. treating said solution with charcoal to obtain a first mixture;
   c. distilling out a portion of said fourth fluid medium from said first mixture to obtain a second mixture comprising a remaining portion of said fourth fluid medium, and crystalline mesotrione;
   d. filtering said second mixture to obtain a first residue comprising said crystalline mesotrione and a first filtrate comprising said remaining portion of said fourth fluid medium;
   e. drying said first residue to obtain a first portion of crystalline mesotrione;
   f. treating said first filtrate with an aqueous alkali solution to obtain a biphasic mixture comprising an aqueous layer comprising metastable form of mesotrione and an organic layer comprising said fourth fluid medium;
   g. separating said aqueous layer from said organic layer;
   h. acidifying said aqueous layer with an acid solution to obtain an acidified aqueous layer and filtering said acidified aqueous layer to obtain said metastable form of mesotrione; and
   i. reiterating steps (a) to (e) to convert said metastable form of mesotrione to crystalline mesotrione.

3. The process as claimed in claim 2, wherein said first filtrate obtained in step (d) is evaporated to obtain a remaining portion of crystalline mesotrione.

4. The process as claimed in claim 1, wherein said alkali metal sulphite is at least one selected from the group consisting of sodium sulphite, potassium sulphite and lithium sulphite.

5. The process as claimed in claim 1, wherein said alkali metal bicarbonate is at least one selected from the group consisting of sodium bicarbonate, potassium bicarbonate, and lithium bicarbonate.

6. The process as claimed in claim 1, wherein the molar ratio of 4-toluene sulfonyl chloride to alkali metal sulphite to alkali metal bicarbonate is in the range of 1:1:2 to 1:1.5:2.5.

7. The process as claimed in claim 1, wherein said alkali metal salt of monochloroacetic acid is at least one selected from the group consisting of sodium monochloroacetic acid, potassium monochloroacetic acid, and lithium monochloroacetic acid.

8. The process as claimed in claim 1, wherein said alkali metal of monochloroacetic acid is prepared from monochloroacetic acid and alkali metal bicarbonate, wherein a molar ratio of monochloroacetic acid to alkali metal bicarbonate is in the range of 1.3:1.1 to 1.3:1.5.

9. The process as claimed in claim 1, wherein said oxidizing agent is at least one selected from the group consisting of sulphuric acid, hydrogen peroxide, sodium hypochlorite, nitric acid and air-Co—Mn catalyst.

10. The process as claimed in claim 1, wherein said first catalyst is vanadium pentoxide.

11. The process as claimed in claim 1, wherein said halogenating agent is thionyl chloride.

12. The process as claimed in claim 1, wherein said first fluid medium is at least one selected from the group consisting of ethylene dichloride and methylene dichloride; and said second fluid medium and said third fluid medium is ethylene dichloride.

13. The process as claimed in claim 1, wherein said second catalyst is at least one selected from the group consisting of tetrabutylammonium bromide, tetramethyl ammonium chloride, triethylbenzyl ammonium chloride, and triphenylphosphonium bromide.

14. The process as claimed in claim 1, wherein said base is at least one selected from the group consisting of triethylamine, sodium hydride, and 1,2,4-triazole.

15. The process as claimed in claim 1, wherein said cyanide ion source is at least one selected from the group consisting of acetone cyanohydrin, sodium cyanide, potassium cyanide, and hydrogen cyanide.

16. The process as claimed in claim 2, wherein said fourth fluid medium is ethylene dichloride.

17. The process as claimed in claim 2, wherein said alkali is at least one selected from the group consisting of triethylamine, sodium hydroxide, and potassium hydroxide.

18. The process as claimed in claim 2, wherein said acid is at least one selected from the group consisting of citric acid, hydrochloric acid, and sulphuric acid.

\* \* \* \* \*